United States Patent
Gelblum et al.

(10) Patent No.: US 6,806,396 B2
(45) Date of Patent: Oct. 19, 2004

(54) DISPOSAL OF FLUOROFORM (HFC-23)

(75) Inventors: Peter Gideon Gelblum, Philadelphia, PA (US); Velliyur Nott Mallikarjuna Rao, Wilmington, DE (US); Charles Joseph Noelke, Wilmington, DE (US); Norman Herron, Newark, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 134 days.

(21) Appl. No.: 10/320,143

(22) Filed: Dec. 16, 2002

(65) Prior Publication Data

US 2003/0166981 A1 Sep. 4, 2003

Related U.S. Application Data

(60) Provisional application No. 60/341,640, filed on Dec. 18, 2001.

(51) Int. Cl.[7] .......................... C07C 17/26; C07C 17/38; C07C 21/00; C07C 21/02; C07C 21/19; C07C 21/22; C07C 17/02; C07C 17/04; C07C 17/08; C07C 21/18

(52) U.S. Cl. ....................... 570/237; 570/153; 570/159; 570/170; 570/171; 570/216; 570/257; 570/261

(58) Field of Search .................................. 570/237, 153, 570/159, 170, 171, 216, 257, 261

(56) References Cited

U.S. PATENT DOCUMENTS

| | | |
|---|---|---|
| 3,009,966 A | 11/1961 | Hauptschein et al. |
| 3,202,720 A | 8/1965 | Hauptschein et al. |
| 5,516,947 A | 5/1996 | Manogue et al. |
| 6,025,532 A | 2/2000 | Sage et al. |

FOREIGN PATENT DOCUMENTS

| | | |
|---|---|---|
| GB | 1076699 | 7/1967 |
| WO | 96/29296 | 2/1996 |

*Primary Examiner*—Elvis O. Price

(57) ABSTRACT

The present invention relates to the co-pyrolysis of fluoroform and chlorodifluoromethane to form a mixture of useful fluoroolefin and saturated HFCs, notably, tetrafluoroethylene and hexafluoropropylene and $CF_3CHF_2$ and $CF_3CHFCF_3$, respectively.

14 Claims, No Drawings

DISPOSAL OF FLUOROFORM (HFC-23)

This application claims the benefit of Provisional Application No. 60/341,640, filed Dec. 18, 2001.

BACKGROUND OF THE INVENTION

1. Field of the Invention

This invention relates to the disposal of $CHF_3$.

2. Description of Related Art

Fluoroform ($CHF_3$, HFC-23) is a by-product of the reaction of HF with trichloromethane to form chlorodifluoromethane ($CHF_2Cl$, HCFC-22), which is the primary source of perfluoroolefin, such as tetrafluoroethylene (TFE). The fluoroform by-product constitutes less than about 3 wt % of the HCFC-22 formed, but because annual production of HCFC-22 is large worldwide, the amount of fluoroform by-product made amounts to several millions of pounds per year. The fluoroform by-product either has to be used or has to be subject to disposal.

U.S. Pat. No. 3,009,966 discloses that fluoroform is thermally inert (col. 1, I. 13–14), but nevertheless finds a use for the fluoroform as a source of TFE and hexafluoropropylene (HFP) by pyrolysis of the fluoroform at temperatures of 700–1090° C., with temperatures of 1000° C. and higher being required to obtain conversions of at least 50% for the fluoroform at contact (pyrolysis times) of 0.1–0.12 sec. (Tables 1 and 2). The higher yields of HFP are accompanied by increasing amounts of perfluoroisobutylene (PFIB), which is toxic. Even at lower pyrolysis temperatures, the yields of PFIB can be quite high. U.S. Pat. No. 6,025,532 discloses the pyrolysis of fluoroform to a mixture of HF, TFE and HFP at a temperature of at least 700° C., but actually at 1000° C. at a contact time of 32 milliseconds (Examples), followed by contacting the mixture with a fluorination catalyst to obtain HFC-125 ($CF_3CHF_2$) and/or HFC-227ea ($CF_3CHFCF_3$). The high temperature required for pyrolyzing fluoroform at short contact times has limited the use of fluoroform by-product, whereby excess fluoroform has been available, which to avoid venting to the atmosphere has been disposed of by incineration.

Several references disclose the use of fluoroform in an auxiliary pyrolysis role. WO 96/29296 discloses the co-pyrolysis of HCFC-22 with fluoroalkane to form primarily large molecule fluoroalkanes. In particular, the reference discloses this reaction being carried out wherein the fluoroalkane co-reactant is fluoroform and the pyrolysis temperature is 700° C. and the contact time is 10 seconds, to obtain 100% conversion of the HCFC-22, with the result being a 60% yield of pentafluoroethane (Example 1). The disadvantage of this process, besides the extraordinarily long contact time, is that 40% of the yield is apparently not useful product. It is impractical to attempt to dispose of HFC-23 by consuming it in a process which produces such a high yield of by-product which itself needs disposal. Example 1 also reports that perfluoropropene is formed, without quantifying its amount, which is characteristic of reporting trace amounts detectable in the gas phase chromatography analysis used. The Examples of this reference are conducted with an aqueous alkaline wash of the pyrolysis reaction mixture to eliminate the HCl co-produced. The washing could also limit the ultimate reaction product to saturated HFC compounds. In the Examples the reactor is quartz. Quartz reacts with hydrogen fluoride, a probable intermediate in the pyrolysis reaction of HFC-23 and HCFC-22. The elements of hydrogen fluoride are part of the process according to the present invention and its consumption in side reactions, as with quartz, would lead to a reduction in the production of saturated hydrofluorocarbons.

Another reference disclosing the auxiliary use of fluoroform in a pyrolysis reaction is U.S. patent application Ser. No. 09/878,540, filed Jun. 11, 2001 (U.S. patent application Publication Ser. No. 2002/0032356-A), which discloses the pyrolysis of HCFC-22 in a gold-lined reactor to direct the synthesis reaction to the formation of the fluoroolefins TFE and HFP, without forming significant amounts of PFIB. The Examples disclose the co-pyrolysis of HCFC-22 and HCFC-124 ($CF_3CHFCl$) to favor the formation of HFP over TFE. The possibility of fluoroform ($CHF_3$) being present with the HCFC-22 is also disclosed as a recycle gas in the reactor system, the fluoroform thereby being the major component fed to the reactor, indicating that the fluoroform is acting as an inert carrier in the pyrolysis process, as would be expected from the relatively low pyrolysis temperatures and short contact times disclosed. Such use of fluoroform is not an effective way to dispose of fluoroform.

The problem remains of finding an economically acceptable use for the fluoroform by-product so that it does not have to be incinerated.

BRIEF SUMMARY OF THE INVENTION

The present invention solves this problem by consuming fluoroform (HFC-23) to economically produce useful product by co-pyrolyzing the fluoroform with chlorodifluoromethane (HCFC-22) at a temperature in the range of about 625–800° C., preferably about 690–775° C. and contact time of less than two seconds, and obtaining as a result thereof a product mixture of useful saturated and unsaturated compounds, i.e. at least three compounds selected from the group consisting of pentafluoroethane ($CF_3CHF_2$, HFC-125), heptafluoropropane ($CF_3CHFCF_3$, HFC-227ea), TFE, and HFP, respectively. The process can be carried out by feeding the mixture of reactants (HCFC-22 and HFC-23) through a reaction zone, the surface of which is metal, preferably gold, to minimize the formation of perfluoroisobutylene by-product in the pyrolysis reaction.

Unexpectedly, the HFC-23 pyrolyzes at the relatively low temperature of the co-pyrolysis reaction in short contact times to produce a high yield, e.g. at least 80%, of the above-mentioned useful products and little to no detectable PFIB. Apparently, the presence of the HCFC-22 in the pyrolysis reaction reduces the reaction (decomposition) temperature of the HFC-23 so that the latter is consumed in the pyrolysis reaction. Typically at least 4 parts by weight of HFC-23 is consumed for each 100 parts by weight of HCFC-22 such that the amount of HFC-23 consumed is greater than the amount produced as by product during the manufacture of HCFC-22.

The function of the fluoroform in the present invention is to increase the amount of useful saturated two- and three-carbon atom compounds, $CF_3CHF_2$ (HFC-125) and $CF_3CHFCF_3$ (HFC-227ea), along with production of TFE and HFP.

DETAILED DESCRIPTION OF THE INVENTION

The pyrolysis reaction in the present invention is carried out by continuous feeding of the co-reactants to a pyrolysis reactor and continuously withdrawing the resultant mixture of reaction products and unreacted reactants from the reactor. Pyrolysis reactors generally comprise three zones: a) a preheat zone, in which reactants are brought close to the reaction temperature; b) a reaction zone, in which reactants reach reaction temperature and are at least partially pyrolyzed, and products and any by-products form; c) a quench zone, in which the stream exiting the reaction zone is cooled to stop the pyrolysis reaction, preferably to 500° C. or lower, to reduce coking or polymerization downstream of the reaction zone. "Coke" is solid carbonaceous material that accumulates in, and on the surface of, the reactor. The resulting fouling is undesirable because it interferes with heat transfer and fluid flow. Quenching may be accomplished by interior cooling or exterior cooling, or both.

The reactor can be tubular, wherein the pyrolysis reaction occurs in the interior of the tube, and the tube can have a variety of cross-sectional shapes, such as circular, oval (elliptical) or polygonal, said shapes being of the interior or of the exterior surfaces of the tube, or both. The tubular reactor will typically have an inner diameter in the case of circular cross-section of at least about 0.125 in (0.32 cm), preferably about 0.125 in (0.32 cm) to about 3 meters, more preferably about 0.5 in (1.27 cm) to about 2 m, and most preferably about 0.7 in (1.8 cm) to about 1 m. The ratio of volume to surface area of a tubular reactor of unit length and of interior radius $R$ can be determined by dividing the surface area $A$ ($A = 2\pi R$) into the volume $V$ ($V = \pi \cdot R2$). If $R$ is in centimeters, $V/A = (R/2)$ cm3/cm2. In this way it can be stated that the volume to surface ratio is at least about 0.08 cm3/cm2, preferably about 0.08 cm3/cm2 to about 75 cm3/cm2, more preferably about 0.32 cm3/cm2 to about 50 cm3/cm2, and most preferably about 0.64 cm3/cm2 to about 25 cm3/cm2.

The reactor is made of metal, such as nickel or nickel alloy. The exposed surface of the reaction zone in particular is of a metal that resists corrosion at the pyrolysis temperatures of reaction of HCFC-22 and HFC-23. Nickel or nickel alloys such as Inconel® or Hastelloy® are preferred, Inconel® is more preferred. Most preferred is gold, because gold is more resistant to the corrosive action of hydrogen halides and the formation of coke than are nickel-based materials. Gold has the further advantage of suppressing PFIB formation. Whereas the process of this invention with a nickel or nickel alloy reactor generates less than about 5% PFIB based on the combined weight of TFE, HFP, HFC-125 and HFC-227ea, in a gold reactor less than about 2% PFIB is formed on the same basis. "Exposed surface" refers to the surface that is exposed to the reactants and/or reaction products in the reaction zone. Apart from using gold as the material of the surface of the reaction zone and optionally of the exposed surface of the quench zone, the reactor can be of conventional design.

The gold on the interior surface of the reaction zone must be supported by a heat-resistant, thermally conductive material of construction, such as a metal which has a melting temperature of at least about 1100° C. and which gives structural integrity to the reactor. Inconel® and Hastelloy® are nickel alloys suitable for use as supporting materials for the gold lining of the reactors (see for example U.S. Pat. No. 5,516,947). Other thermally conductive supporting materials can be used. Thermal conductivity enables the reactor to be externally heated to provide the interior temperature necessary for the pyrolysis reaction. It is desirable that the supporting material be metallurgically bonded to the gold lining for the best heat transfer. By a metallurgical bond is meant a bond in which atoms of the metals in the supporting material and the gold lining interdiffuse, that is, diffuse among each other about the bonded interface. U.S. patent application Publication Ser. No. 2001/0046610 (Nov. 29, 2001) discloses a method for making a gold-lined tube in which the gold lining is metallurgically bonded to the supporting material.

Normally a plurality of the tubular reactors will be positioned within a shell, and a heating medium will be flowed between the interior wall of the shell and the exterior walls of the tubular reactors bundled therein to provide the heating for the pyrolysis reaction. Alternatively, the shell can be exteriorly heated or fired by means such as electrical means to provide the interior heating. The combination of the shell and the tubular reactors positioned therein forms the pyrolysis furnace. Alternatively, the reactor may consist of a single reaction vessel, where the required heat for the reaction is other means such as hot inert gas mixed with the reactants. Use of hot inert gas to supply some or all of the heat needed for the reaction reduces or eliminates the heat that must be supplied through the reactor wall. Supplying heat through the reactor wall requires that the wall be hotter than the contents of the reaction space. This condition can lead to undesirable reactions and to decomposition of reactants, intermediates, or products at the wall. The greater the reactor cross-section, the higher wall temperatures must be to supply the necessary heat. Therefore, heating by means of hot inert gas becomes more attractive as the reactor cross-section increases. Examples of hot inert gases which can be used include helium and tetrafluoromethane.

Preferably, the residence time (contact time) in the reaction zone is less than about 1.5 seconds, and more preferably the residence time is about 0.01 to about 1 seconds and even more preferably, from about 0.05 to about 0.8 seconds. Residence time is determined by dividing the net volume of the reaction zone by the volume feed rate in seconds of the gaseous feed to the reactor at reaction temperature and pressure.

The gas temperature within the reaction zone is considered to be the pyrolysis reaction temperature and is measured using a thermocouple in the gas phase in the reaction zone. The reaction zone is heated to a temperature sufficient for the pyrolysis reaction to occur, preferably within the reaction time of less than 1.5 seconds.

Preferably, the HCFC-22 and HFC-23 are preheated to temperatures approaching but not reaching the temperatures at which their respective pyrolyses begin. Preheating reduces the amount of heat that must be provided in the reaction zone and thereby reduces the temperature difference between the walls of the reaction zone and the gas feed. The closer the wall and the gas temperatures are to the desired reaction temperature, the fewer will be side reactions generating undesirable products and reactor fouling. HCFC-22 and HFC-23 may be mixed and preheated together. The preferred preheating temperature when the two gases are fed together is between about 500° C. and 600° C., and most preferably between about 550° C. and 600° C. If the gases are preheated separately the HCFC-22 is preheated to about 300° C. to 450° C., and the HFC-23 is preheated to about 500° C. to 600° C.

In another embodiment in which HFC-23 and HCFC-22 are preheated separately, the HFC-23 is preheated to at least about 850° C., and the HCFC-22 is preheated to about 300° C. to 550° C. This embodiment is preferred for adiabatic reaction of HFC-23 and HCFC-22 or to reduce the amount of heat that must be supplied to the reaction by heating the reaction vessel. It takes advantage of the thermal stability of HFC-23 to heat it to less than its decomposition temperature (e.g. conversion of no more than 3%) in the absence of HCFC-22. The heat in the HFC-23 supplies some or all of the heat necessary for the reaction of HFC-23 with HCFC-22 and reduces or eliminates the need for heat to be provided to the reaction vessel. The quantity of heat provided will depend upon the amount of HFC-23 in relation to the amount of HCFC-22.

Depending upon contact times and reaction zone temperatures as well as feed ratios, HFC-23 and HCFC-22 may not be consumed completely in a single pass through the reactor. In continuous processes it is often most efficient to operate at less than 100% conversion so as to maximize production of desired products and minimize undesirable products and fouling. When conversion is less than 100% in the process of this invention, the stream exiting the reactor is treated by conventional methods such as distillation to separate products from unreacted reactants, and the unreacted reactants are mixed with fresh HFC-23 and HCFC-22 to bring the resulting mixture to the desired composition, and the mixture is fed back into the reactor. It may also be desirable to recycle some of the products. For example, $CF_3CFHCl$ (HCFC-124), $CF_2ClCF_2H$ (HCFC-124a), and octafluorocyclobutane (($CF_2$)$_4$, c318) if formed, can be separated from other products such as HFC-125, HFC-227ea, TFE, and HFP, and added to the reactor feed mixture. Pyrolysis of HCFC-124 and HCFC-124a in the presence of HCFC-22 and HFC-23 contributes to the production of HFP. c318 contributes to TFE production. Through recycling, more HFC-23 can be consumed than is produced in the original manufacture of HCFC-22.

In another embodiment, the flow of the feed through the reactor is partially obstructed to cause back-mixing, i.e. turbulence, and thereby promote mixing of reactants and good heat transfer, further reducing the necessary residence time of the feed in the reactor, e.g. to less than about one-half second. This partial obstruction can be conveniently obtained by using perforated baffles or packing. Increased back-mixing can also be accomplished by increasing the feed rate so as to cause turbulent flow through the reactor.

The volume ratios of HFC-23:HCFC-22 are preferably about 1:10 to 5:1. One preferred ratio is about 2:1 to 5:1, more preferred being about 2:1 to 4:1. Another preferred ratio is no greater than 1:1, such as 1:10 to 1:1. Unreacted HFC-23, is recovered and recycled along with the unconverted HCFC-22. Enough fresh HFC-23 and HCFC-22 are added to this recycle stream to make up for the material converted in the reactor. Preferably the residence time in the reaction zone (contact time), and the relative proportions of HCFC-22 and HFC-23, are such that overall conversion is at least about 10% and yield to useful products is at least about 90%.

HFC-125 finds use as a refrigerant and HFC-227ea finds use as a propellant and fire extinguishant.

The reactor is operated at a temperature, residence time and HFC-23:HCFC-22 ratio such that at least 3 parts of the HFC-23 is converted relative to 100 parts of HCFC-22 converted in order that the amount of HFC-23 consumed is greater than the amount of HFC-23 produced as a by-product during the manufacture of HCFC-22 and which HFC-23 is usually less than about 3 wt %.

EXAMPLES

The reactor used herein is a ¾ inch (1.9 cm) inner diameter (ID) gold-lined reactor. The reactor outer tube material is a 16 inch (40.6 cm) length Inconel® 600 (nickel alloy) tube with a wall thickness of 0.113 inch (0.29 cm) and an outer diameter (OD) of 1.046 inch (2.7 cm). The inner tube material is gold, metallurgically bonded to the Inconel® as described in Example 1 of U.S. patent application Publication Ser. No. 2001/0046610 (Nov. 29, 2001). The wall thickness of the gold tube is 0.039 inch (0.1 cm) and the tube ID is 0.742 inch (1.9 cm). Prior to using this tube, an 8 inch (20.3 cm) portion (centered in the 16 inch (40 cm) length) is milled to an OD of 15/16 inch (2.4 cm) so that 1 inch (2.5 cm) ID clamp-on heaters fit snugly with enough room to position thermocouples that control and monitor temperatures. The preheat zone is 5 inch (13 cm) long and the reaction zone is 2 inch (5 cm) long. They are heated by a ceramic-type band heaters. Temperatures are controlled using thermocouples positioned at the center of each section on the outside wall of the tube. They are held securely in place by the heaters themselves. In addition, the corresponding gas temperature inside the reaction zone is also measured. Gas feeds to the reactor are controlled using calibrated mass flowmeters. The reactor is operated at about 1–2 psig (108–115 kPa) back-pressure to get flow through the analytical system.

A small portion of the product stream from the reactor is analyzed using an on-line GC/MS (gas chromatograph/mass spectrometer) equipped with a 20 foot (6.1 m)×0.125 inch (3.2 mm) steel column packed with 5% Krytox® 143AC perfluoroether on 60/80 mesh (0.25/0.18 mm) Carbopak BHT. GC programming conditions are set for a start temperature of 60° C. which is held for 3 minutes. It is then heated to 200° C. at the rate of 5° C./minute and held at 200° C. for 5 minutes. The analytical results are reported in mole %. In the examples, product analysis shows less than 2 wt % PFIB based on the total weight of TFE, HFP, HFC-125, and HFC-227ea unless otherwise stated.

The identification and structure of fluorocarbons disclosed herein are listed below.

| | | | |
|---|---|---|---|
| HCFC-22 = | $CHF_2Cl$ | HFC-23 = | $CHF_3$ |
| HFC-125 = | $CF_3CF_2H$ | HFC-227ea = | $CF_3CHFCF_3$ |
| HFC-227ca = | $CF_3CF_2CF_2H$ | TFE = | $CF_2{=}CF_2$ |
| c318 = | $cyclo(CF_2)_4$ | HFP = | $CF_2{=}CFCF_3$ |
| HCFC-124 = | $CF_3CFHCl$ | HCFC-124a = | $CF_2ClCF_2H$ |
| HCFC-226cb = | $CF_2ClCF_2CF_2H$ | FC-1318 = | $C_4F_8$ isomer not PFIB |
| PFIB = | $(CF_3)_2C{=}CF_2$ | | |

Example 1

Through the reactor maintained at an operating control temperature setting of 775° C. and a preheater temperature setting of 600° C., a stream of HFC-23 is passed at flowrates of 800, 400, 200, and 100 cc/min at standard temperature and pressure (sccm). At the operating flowrates of 400, 200, and 100 sccm, the conversion of HFC-23 to TFE is about 0.2, 0.4, and 0.6% respectively. Only traces of HFP, HFC-125 and HFC-227ea are observed. The gc detection limit is about 1000 ppm.

Conclusion: When HFC-23 is the sole feed to the reactor at 775° C., >99 mole % of HFC-23 is unreacted, and only TFE is formed in measurable quantities in the little reaction that does occur. Other small amounts of byproducts produced were less than 0.2 mole % of the total.

Example 2

Through the reactor maintained at a control temperature setting of 850° C. and a preheater setting of 600° C., a stream of HFC-23 is passed at flowrates of 400, 200 and 100 sccm. The conversion of HFC-23 to TFE is 0.9, 2.0 and 3.0% respectively. Also observed are 0.2 and 0.6% HFP at HFC-23 flowrates of 200 and 100 sccm. At the HFC-23 operating flowrate of 100 sccm, 0.15% HFC-125 is obtained which corresponds to less than 5% of the total of TFE and HFC-125. Perfluoroisobutylene (0.08%) is also identified by GC/MS at this low-flow condition.

Conclusion: Even at a reactor control temperature setting of 850° C., when HFC-23 is the sole feed to the reactor, conversion is only from about 1 to 5 mole % and 95% of the product that forms is TFE and HFP. HFC-125 production is <5% of the product and HFC-227ea is less than 1%.

Examples 3–6

Through the reactor, operating at a control temperature setting between 775° C. and 850° C. and a preheat temperature of 600° C. is passed an equimolar flow of HFC-23 and HCFC-22 at the rates indicated in Table 1. The major products of the reaction, and the combined unconverted HCFC-22 and HFC-23 starting materials are shown in Table 1. Contact time for these Examples is about 1 second.

TABLE 1

| Example Number | 3 | 4 | 5 | 6 |
|---|---|---|---|---|
| Reactor control temp. setting (° C.) | 775 | 825 | 850 | 850 |
| Reactor gas temperature (° C.) | 697 | 735 | 751 | 747 |
| HCFC-22 feed (cc/min) | 100 | 100 | 100 | 200 |
| HFC-23 feed (cc/min) | 100 | 100 | 100 | 200 |
| Results (mole %) | | | | |
| TFE | 9.80 | 5.51 | 5.05 | 11.80 |
| HFC-125 | 0.68 | 2.89 | 3.86 | 1.45 |
| HFP | 1.94 | 4.88 | 6.08 | 3.11 |
| HFC-227ea | ND | 1.80 | 2.25 | 0.80 |
| HCFC-124a | 3.16 | 4.21 | 3.75 | 3.45 |
| HCFC-124 | 0.29 | 0.75 | 0.80 | 0.52 |
| c318 | 2.99 | 2.02 | 1.33 | 2.57 |
| PFIB | 0.05 | 0.18 | 0.26 | 0.10 |
| FC-1318 | 0.07 | 0.25 | 0.40 | 0.14 |
| HCFC-226cb | 0.67 | 0.49 | 0.33 | 0.45 |
| HFC-23 + HCFC-22 | 79.5 | 75.3 | 73.6 | 74.6 |
| 125/(125 + TFE) × 100 | 6.5 | 34.4 | 43.3 | 10.9 |
| 227ea/(227ea + HFP) × 100 | — | 26.9 | 27.0 | 20.5 |

ND = Less than 100 ppm by total volume.

Conclusion: Compared to the pyrolysis of HFC-23 alone in Examples 1 (reactor control temperature setting 725° C.) and 2 (reactor control temperature setting 850° C.), pyrolysis in the presence of HCFC-22 gives 0.7% HFC-125 at reactor control temperature setting 725° C. (reactor gas temperature 697° C.), where none was detectable in Example 1, and 3.9% HFC-125 at 850° C. (reactor gas temperature 750° C.), compared to 0.15% in Example 2. The presence of HCFC-22 promotes the pyrolysis of HFC-23 and the formation of HFC-125 and HFC-227ea. If necessary or desired, the HCFC-124, HCFC-124a, and c318 can be recovered as products or recycled back to the reactor to produce additional quantities of TFE and HFP.

Examples 7–14

In these examples, the ratio of HFC-23:HCFC-22 is varied in addition to the reactor control temperature. The preheater setting is 600° C.?. The results summarized in Table 2 show the reaction products obtained. Contact time for these Examples is about 0.5 second.

TABLE 2

| Example Number | 7 | 8 | 9 | 10 | 11 | 12 | 13 | 14 |
|---|---|---|---|---|---|---|---|---|
| Reactor Control temperature Setting (° C.) | 775 | 775 | 825 | 825 | 825 | 850 | 850 | 850 |
| Reactor gas temperature (° C.) | 692 | 694 | 729 | 729 | 731 | 746 | 750 | 746 |
| HFC-23 feed (cc/min) | 300 | 350 | 250 | 300 | 350 | 250 | 300 | 350 |
| HCFC-22 feed (cc/min) | 100 | 50 | 150 | 100 | 50 | 150 | 100 | 50 |

TABLE 2-continued

| Example Number | 7 | 8 | 9 | 10 | 11 | 12 | 13 | 14 |
|---|---|---|---|---|---|---|---|---|
| Results (mole %) | | | | | | | | |
| TFE | 7.71 | 2.77 | 9.31 | 6.47 | 2.71 | 8.46 | 6.01 | 2.87 |
| HFC-125 | 0.35 | 0.16 | 1.06 | 0.86 | 0.31 | 1.52 | 1.44 | 0.45 |
| HFP | 0.62 | 0.17 | 1.93 | 1.17 | 0.30 | 2.45 | 1.71 | 0.41 |
| HFC-227ea | 0.15 | 0.09 | 0.58 | 0.48 | 0.16 | 0.84 | 0.79 | 0.22 |
| HCFC-124a | 0.45 | 0.03 | 1.04 | 0.71 | 0.03 | 1.99 | 0.82 | 0.03 |
| HCFC-124 | 0.05 | 0.01 | 0.09 | 0.12 | 0.02 | 0.34 | 0.17 | 0.02 |
| c318 | 0.66 | 0.10 | 1.72 | 0.89 | 0.15 | 1.63 | 0.89 | 0.18 |
| HFC-23 + HCFC-22 | 90.0 | 96.7 | 84.3 | 89.3 | 96.3 | 82.8 | 88.2 | 95.8 |
| 125/(TFE + 125) × 100 | 4.3 | 5.4 | 10.2 | 11.7 | 10.3 | 15.2 | 19.3 | 13.6 |
| 227ea/(HFP + 227ea) × 100 | 19.4 | 34.6 | 23.1 | 29.1 | 34.8 | 25.5 | 31.6 | 32.8 |

Conclusion: Increasing the ratio of HFC-23 to HCFC-22 in the feed from 1:1 (see Example 6 in Table 1) through 5:3 favors formation of HFC-125 and HFC-227ea over TFE and HFP. Conversion declines at the expense of the fluoroolefins until, at 7:1, conversion to HFC-125 and HFC-227ea declines also although the amount of HFC-125 and HFC-227ea, relative to TFE and HFP respectively increases.

Examination of the data summarized in Table 2 and comparison with Table 1 shows that at a given operating temperature, the amount of HFC-125 and HFC-227ea that can be coproduced can be varied by varying the HCFC-22:HFC-23 ratio. Again, comparison of the results with that obtained with Example 2 shows that the yields of HFC-125 and HFC-227ea relative to TFE and HFP respectively are higher when HCFC-22 is present in the feed along with HFC-23.

Examples 15–18

Examples are run in a gold-lined quartz TGA (thermogravimetric analyzer) type flow reactor (a 1 in (2.54 cm) diameter quartz tube lined with gold foil) packed with prefluorinated 2 mm gamma alumina spheres. The selective preheat of the reactants fed the HFC-23 is preheated to 600° C. and HCFC-22 to 400° C. The ratio of HCFC-22:HFC-23 is varied and so is the total flow rate and the wall temperature. The contact time for these Examples is less than 0.5 seconds. The results in Table 3 describe the reaction products. The remainder is essentially unreacted HCFC-22 and HFC-23.

TABLE 3

| Example Number | 15 | 16 | 17 | 18 |
|---|---|---|---|---|
| Reactor wall temp. (° C.) | 775 | 775 | 850 | 850 |
| Reactor gas temperature (° C.) | 704 | 693 | 768 | 753 |
| HCFC-22 feed (cc/min) | 106 | 250 | 106 | 250 |
| HFC-23 feed (cc/min) | 519 | 750 | 519 | 750 |
| Results (mole %) | | | | |
| TFE | 20.2 | 19.5 | 17.9 | 24.6 |
| HFC-125 | 0.9 | 0.3 | 3.1 | 1 |
| HFP | 2.3 | 1.2 | 8.1 | 3.6 |
| HFC-227 | 2.1 | 1.4 | 3.4 | 2 |
| HCFC-124a | 0.6 | 0.3 | 0.7 | 0.4 |
| c318 | ND | ND | 0.1 | 0.05 |
| PFIB | ND | ND | 0.07 | 0.35 |
| HFC-23 + HCFC-22 | 71.5 | 76.8 | 61.3 | 64.5 |
| 125/(125 + TFE) × 100 | 4.3 | 1.5 | 14.8 | 3.9 |
| 227/(227 + HFP) × 100 | 47.7 | 53.8 | 38.6 | 46.3 |
| Conversion of HCFC-22 | 82.9 | 59.6 | 92.9 | 81.6 |
| Conversion of HFC-23 | 17.4 | 11.1 | 27.6 | 20.1 |

ND = less than 100 ppm. HFC-227 is a combination of the isomers HFC-227ea and HFC-227ca.

Under these conditions, the yield of the saturated compounds are high and the yield of HFC-227 is much higher than the yield of HFC-125.

What is claimed is:

1. A process for disposing of fluoroform by consuming it by co-pyrolyzing a reaction mixture of said fluoroform and chlorodifluoromethane at a temperature in the range of about 625–800° C., and contact time of less than about two seconds and obtaining as a result thereof a product mixture comprised of at least three compounds selected from the group consisting of tetrafluoroethylene (TFE), hexafluoropropylene (HFP), pentafluoroethane ($CF_3CHF_2$), and heptafluoropropane ($CF_3CHFCF_3$).

2. The process of claim 1 carried out by feeding said reaction mixture through a reaction zone, the surface of which is of metal.

3. The process of claim 2 wherein said metal is gold.

4. The process of claim 1 wherein the molar ratio of said fluoroform to said chlorodifluoromethane is at least about 5:1 to about 2:1 to maximize the proportion of $CF_3CHF_2$ and $CF_3CHFCF_3$ formed relative to the formation of said TFE and HFP.

5. The process of claim 1 wherein the molar ratio of said fluoroform to said chlorodifluoromethane is no greater than about 1:1 to maximize the proportion of TFE and HFP formed relative to the formation of said $CF_3CHF_2$ and $CF_3CHFCF_3$.

6. The process of claim 1 wherein less than about 5% perfluoroisobutylene, based on the combined weight of said compounds is formed.

7. The process of claim 3 wherein less than about 2% perfluoroisobutylene, based on the combined weight of said compounds, is formed.

8. The process of claim 1 wherein the product mixture contains fluoroform, separating said fluoroform from the product mixture and adding the resultant fluoroform to said reaction mixture.

9. The process of claim 1 wherein the product mixture contains HCFC-124, HCFC-124a, and c318, separating said HCFC-124, HCFC-124a, and c318 from the product mixture and adding the resultant HCFC-124, HCFC-124a, and c318 to the reaction mixture.

10. The process of claim 1 and additionally feeding said fluoroform and said chlorodifluoromethane to said reaction mixture together and at a preheat temperature of about 500–600° C.

11. The process of claim 1 and additionally feeding said fluoroform and said chlorodifluoromethane to said reaction mixture at preheat temperatures of about 500–600° C. and about 300–450° C., respectively.

12. The process of claim 1 and additionally feeding said fluoroform and said chlorodifluoromethane to said reaction mixture at preheat temperatures of at least about 850° C., but less than the decomposition temperature of said fluoroform, and about 300–550° C., respectively.

13. The process of claim 2 wherein said reaction zone contains packing.

14. The process of claim 13 wherein said packing is perfluorinated gamma alumina.

* * * * *